United States Patent [19]
Wätjen et al.

[11] Patent Number: 4,866,065
[45] Date of Patent: Sep. 12, 1989

[54] IMIDAZOTHIENOPYRIMIDINES USEFUL IN PSYCHOPHARMACEUTICAL PREPARATIONS

[75] Inventors: Frank Wätjen; Holger C. Hansen, both of Vaerlose, Denmark

[73] Assignee: A/S Ferrosan, Soborg, Denmark

[21] Appl. No.: 254,421

[22] Filed: Oct. 6, 1988

[30] Foreign Application Priority Data

Oct. 6, 1987 [DK] Denmark .............. 5221/87

[51] Int. Cl.$^4$ .............. A61K 31/505; C07D 495/14
[52] U.S. Cl. .............. 514/267; 544/250; 544/278
[58] Field of Search .............. 544/250; 514/267

[56] References Cited

U.S. PATENT DOCUMENTS

| | | | |
|---|---|---|---|
| 4,376,121 | 3/1983 | Kienzle | 514/267 |
| 4,622,321 | 11/1986 | Wätjen et al. | 514/220 |
| 4,670,433 | 6/1987 | Wätjen et al. | 514/210 |
| 4,703,049 | 10/1987 | Gillespie et al. | 514/258 |
| 4,771,051 | 9/1988 | Wätjen et al. | 514/267 |

FOREIGN PATENT DOCUMENTS

2411274 9/1975 Fed. Rep. of Germany ...... 544/250

*Primary Examiner*—Mukund J. Shah
*Assistant Examiner*—Diana G. Rivers
*Attorney, Agent, or Firm*—Gordon W. Hueschen

[57] ABSTRACT

New heterocyclic compounds having the general formula

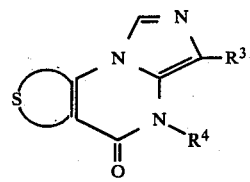

(I)

wherein

R$^3$ is

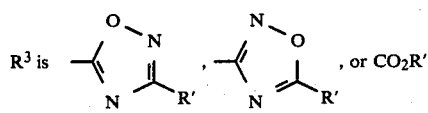

, or CO$_2$R' wherein R' is
C$_{1-6}$-alkyl, C$_{3-7}$-cycloalkyl or C$_{1-6}$-alkoxymethyl;
R$^4$ is C$_{1-6}$-alkyl;
—S— is

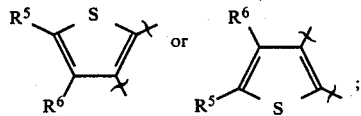

and
wherein R$^5$ and R$^6$ independently are hydrogen, C$_{1-6}$-alkyl, or aryl.

The compounds are useful in psychopharmaceutical preparations as anticonvulsants, anxiolytics, hypnotics, and in improving the cognitive function of the brain of mammals.

7 Claims, No Drawings

IMIDAZOTHIENOPYRIMIDINES USEFUL IN PSYCHOPHARMACEUTICAL PREPARATIONS

The present invention relates to therapeutically active heterocyclic compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of heterocyclic compounds have strong affinity for the benzodiazepine receptors which make them useful in psychopharmaceutical preparations.

Accordingly, it is an object of the invention to provide such novel heterocyclic compounds.

The heterocyclic compounds of the invention have the general formula I

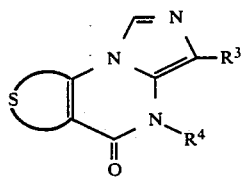    (I)

wherein

R$^3$ is 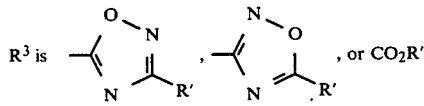, or CO$_2$R' wherein R' is
C$_{1-6}$-alkyl, C$_{3-7}$-cycloalkyl or C$_{1-6}$-alkoxymethyl; R is C$_{1-6}$-alkyl;
—S— is

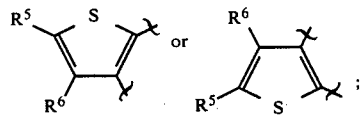

and
wherein R$^5$ and R$^6$ independently are hydrogen, C$_{1-6}$-alkyl, or aryl.

The invention also relates to a method of preparing the above mentioned compounds. This method comprises:

(a) reacting a compound of formula II

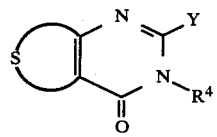    (II)

wherein —S— and R$^4$ have the meanings set forth above and wherein Y is a leaving group, with a compound having the formula III

    (III)

wherein R$^3$ has the meaning set forth above, to form a compound of the invention, or (b) reacting a reactive derivative of a compound having the general formula IV

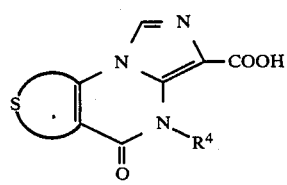    (IV)

wherein —S— and R$^4$ have the meanings set forth above, with a compound having the general formula V

R'—C(C=NOH)NH$_2$    (V)

wherein R' has the meaning set forth above to form a compound of the general formula I wherein R$^3$ is

wherein R' has the meaning set forth above, or (c) reacting a compound having the general formula VI

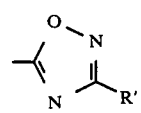    (VI)

wherein —S— and R$^4$ the meanings set forth above, with a compound having the general formula VII

R'—C(OCH$_3$)$_2$N(CH$_3$)$_2$    (VII)

wherein R' has the meaning set forth above, to form a compound having the general formula VIII

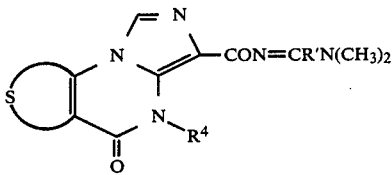

wherein —S— and R⁴ have the meanings set forth above and reacting the compound having the formula (VIII) with NH₂OH or another aminating agent, to form a compound having the general formula I, wherein R³ is

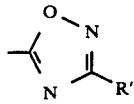

wherein R' has the meaning defined above, or (d) reacting a compound having the general formula IX

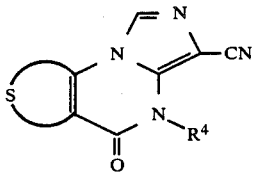

wherein —S— and R⁴ having the meanings set forth above, with NH₂OH to form a compound having the general formula X

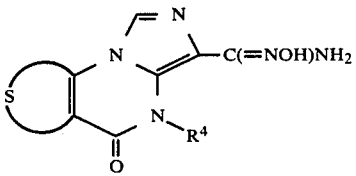

wherein —S— and R⁴ have the meanings set forth above, and reacting the compound having the formula (X) with R'—COCl or (R'CO)₂O wherein R' has the meaning set forth above, to form a compound of formula I, wherein R³ is

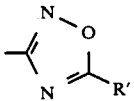

wherein R' has the meaning set forth above.

The leaving group, Y, may be any suitable leaving group and, for example, those disclosed in U.S. Pat. No. 4,031,079 or 4,359,420, for example, halogen, alkylthio, e.g., methylthio, aralkylthio, N-nitrosoalkylamino, alkoxy, mercapto, —OP(O)-(OR)₂ wherein R is lower-alkyl or —OP(O)(NR'R'') wherein R' and R'' each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available benzene derivatives and by using well known synthetic methods and as described in Synthesis, Vol. 10, pp. 681–682.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of flunitrazepam to benzodiazepine receptors in a living brain to be reduced to 50% of the oontrol value.

Such an in vivo test is carried out as follows:

Principle. Twenty minutes after a dose of ³H-flunitrazepam (³H-FNM) (200 μCi/kg, i.v.) the amount of specific ³H-FNM binding to brain benzodiazepine receptors has reached its maximal value. This specific binding of ³H-FNM can be partly or completely prevented by simultaneous or prior administration of pharmacologically active benzodiazepines and by some benzodiazepine-like agents (Chang and Snyder, Eur.J. Pharmacol. 48, 212–218 (1978)).

Test procedure. Suspensions of test substances (2 mg/ml) are prepared in 5% Duphasol-X (TM Duphar, castor oil-ethylene oxide derivative for emulsifying and solubilizing Oil and other water-insoluble substances) by sonification for 10 min using a Branson B15 microtip ultrasonifier (setting 7). Groups of three mice (female, NMR, 18–22 grams) are injected with the test substance at 100 mg/kg intraperitoneally. Fifteen minutes after test substance administration the mice are challenged with 4 μCi intravenously of ³H-FNM (70–90 Ci/mole) in 200 μl physiological saline. Twenty minutes after ³H-FNM administration mice are sacrificed by decapitation, the forebrains rapidly excised (within 30 sec) and homogenized in 12 ml of icecold 25 mM KH₂PO₄, pH 7.1, using an Ultra-Turrax homogenizer fitted with an N 10 shaft. Two aliquots of 1 ml are immediately filtered through Whatman GF/C glassfibre filters and washed with 2×5 ml of the above mentioned buffer. The amounts of radioactivity on the filters are determined by conventional scintillation counting. One group of untreated mice serves as control. One to three mice are injected with 25 μg/kg clonazepam i.p. 30 minutes before ³H-FNM to determine the amount of non-specific 3H-FNM binding, which should be between 8–15% of total binding. When doses of 100 mg/kg inhibit more than 50% of specific ³H-flunitrazepam binding; test substances are administered in doses, which are factors of 3.16 times lower than 100 mg/kg. The $ED_{50}$ for a test substance is defined as that dose which inhibits 50% of specific $^3$H-FNM binding. Specific binding is the amount of binding in controls minus the amount binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25–75%:

$$ED_{50} = \text{(administered dose)} \times \frac{1}{\left[\frac{C_o}{C_x} - 1\right]} \text{ mg/kg}$$

where $C_o$ is specific binding in controls and $C_x$ is specific binding in mice treated with test substance.

Test results obtained by testing some compounds of the invention will appear from the following table I.

TABLE 1

| Compound | $ED_{50}$ (mg/kg) |
|---|---|
| 8 | 0.9 |
| 3 | 0.6 |
| 10 | 1.8 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, t he carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.05–100 mg in a pharmaceutically-acceptable carrier per unit dosage.

A typical tablet which may be prepared by conventional tabletting techniques contains:

Active compound: 1.0 mg
Lactosum: 67.8 mg Ph.Eur.
Avicel TM : 31.4 mg
Amberlite TM IRP 88: 1.0 mg
Magnesii stearas: 0.25 mg Ph.Eur.

Due to their high degree of affinity for the benzodiazepine receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living mammal body, including a human, in need of the same for the treatment, alleviation, amelioration, or elimination of an indication, associated with the central nervous system and the so-called benzodiazepine receptors, which requires such psychopharmaceutical treatment, e.g., especially convulsion and/or anxiety states, if desired in the form of a pharmaceuticallyacceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1–200 milligrams daily, 1–100 milligrams daily, and especially 1–30 milligrams daily. depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1 a. Ethyl 4-methyl-2-(N'-methylureido)thiophene-3-carboxylate

To a stirred ice-cooled solution of ethyl 2-amino-4-methyl-thiophene-3-carboxylate (1,85 g, 10 mmole) and triethyl amine (1,4 ml, 10 mmol) in dry tetrahydrofuran (50 ml) was added dropwise a phosgene solution (11 mmol, in toluene). The mixture was thereafter heated to reflux for 30 min, then cooled to room temperature and exposed to a gaseous stream of methylamine for 5 min. After additional stirring for 15 min, the mixture was filtered and the filtrate was evaporated to give the title compound as white crystals.

$^1$H-NMR (60 MHz, CDCl$_3$) (ppm): (1,5, T 3H), (2,4, S 3H), (2,9, D 3H), (4,4, Q 2H) (5,7, broad NH), (6,2, S 1H) (10,8, broad, NH).

In exactly the same manner ethyl 4-phenyl-2-(N'-methylureido)thiophene-3-carboxylate. m.p. 109°–12° C. and ethyl 2-(N'-ethylureido)-4-phenyl-thiophene-3-carboxylate M.p. 129°–33° C. were prepared from ethyl 2-amino-4-phenyl-thiophene-3-carboxylate (Gewald et. al., Chem. Ber. 99, 94 (1966) and methylamine and ethylamine respectively.

b. 4,5-Dihydro-3,5-dimethyl-6-(5-methyl-1,2,4-oxadiazol-3yl)-4-oxo-imidazo[1,5-a]thieno[3,2-e]pyrimidine A stirred solution of ethyl 4-methyl-2-(N$^1$-methylureido)-thiophene-3-carboxylate (2,3 g), triphenylphosphine (2,62 g), triethylamine (1.4 ml) and carbontetrachloride (5 ml) in CH$_2$Cl$_2$ (50 ml) was refluxed for 30 min, whereafter it was evaporated in vacuo. The oily residue was extracted twice with boiling petrol ether. The combined petrol ether solutions were evaporated to give N-methyl N'-(3-carbomethoxy-4-methyl-thien-2-yl)-carbodiimide as an oil. The presence of the carbodiimide moeity was confirmed by an IR absorbtion band at 2140 cm$^{-1}$.

The oil was used below without any further purification.

To a stirred −30° C. cold solution of potassium-t-butylate (1,13 g) in dry DMF (40 ml) was added 3-isocyanomethyl-5-methyl-1,2,4-oxadiazole (1.4 g). This solution was added to a solution of the above described carbodiimide in dry DMF (20 ml).

The final solution was allowed to attain to room temperature before acetic acid (1 ml) was added. The solvent was removed in vacuo and the oily residue was thereafter partitioned between ethyl acetate (25 ml)/2N HCl (25 ml). The aqueous phase was separated and neutralized with potassium carbonate, whereby the title compound precipitated as oily crystals. The crude product was purified by SiO$_2$ fractionation with ethyl acetate/methanol-9:1 as eluent.

This treatment left the title compound as pale crystals. M.p. 207°–208° C. (Compound 1).

EXAMPLE 2 a. Methyl 3-(N'-methylureido)thiophene-2-carboxylate

To a stirred solution of methyl-3-amino-thiophene-2-carboxylate (5 g, 31,8 mmole) and triethylamine (4,43 ml, 31,8 mmole) in dry tetrahydrofuran (100 ml) was added dropwise a 20% phosgene solution in toluene (31,8 mmole). After the addition had been completed the mixture was heated to reflux for 30 min, followed by filtration at room temperature. The filtrate was evaporated in vacuo, whereafter the crystalline residue was suspended in water (200 ml). Filtration of the suspension left the title compound as white crystals. M.p. 141°–142° C.

b. 1,2,3,4-Tetrahydro-3-methyl-2,4-dioxo-thieno[3,2-d]pyrimidine

Methyl 3-(N'-methylureido)thiophene-2-carboxylate (4,2 g, 20 mmol) was suspended with stirring in 5% aqueous potassium hydroxide (50 ml). Dimethylformamide was added until a clear solution was obtained. Stirring was continued for 30 min, whereafter the solution was neutralized with acetic acid. This afforded a crystalline precipitate of the title compound, which was separated by filtration and washed with water. M.p. > 300° C.

In a similar manner the following compounds were prepared:

1,2,3,4-tetrahydro-3-methyl-2,4-dioxo-5-phenyl-thieno[2,3-d]-pyrimidine, m.p. 260°–262° C., from ethyl 2-(N'-methylureido)-4-phenyl-thiophene-3-carboxylate 3-ethyl-1,2,3,4-tetrahydro-2,4-dioxo-5-phenyl-thieno[2,3-d]-pyrimidine, m.p. 255°–260° C., from ethyl 2-(N'-ethylureido)-4-phenyl-thiophene-3-carboxylate c. Ethyl 4,5-dihydro-4-methyl-5-oxo-imidazo[1,5-a]thieno-[2,3-e]pyrimidine-3-carboxylate Solution A:

To a stirred solution of 1,2,3,4-tetrahydro-3-methyl-2,4-dioxo-thieno[3,2-d]pyrimidine (2,73 g, 15 mmole) in dry DMF (30 ml) was added sodium hydride (0,8 g 55% in mineral oil, 20 mmole). After stirring for 20 min the solution was cooled to 0° C. and chlorodiethyl phosphate (2,87 ml, 20 mmole) was added. Stirring at 0° C. was continued for 20 min, whereafter solution B was added (see below).

Solution B:

To a −30° C. cold stirred solution of potassium t-butylate (2,25 g, 20 mmole) in dry DMF (20 ml) was added ethyl iso-cyanoacetate (2,3 ml, 20 mmole). After stirring for 5 min the solution was added to solution A.

The final mixture was allowed to attain to room temperature before it was poured into water (100 ml). Acetic acid wa added to neutral pH. The precipitated crude product was collected by filtration and purified by treatment with hot ethanol. M.p. 258°–259° C. (Compound 2).

In a similar manner the following oompounds were prepared: 3-(5-cyclopropyl-1,2,4-oxadiazol-3-yl)-4,5-dihydro-4-methyl-5-oxo-imidazo[1,5-a]thieno[2,3-e]pyrimidine, m.p. 178°–179° C. from 1,2,3,4-tetrahydro-3-methyl-2,4-dioxo-thieno[3,2-d]pyrimidine and 5-cyclopropyl-3-isocyanomethyl-1,2,4-oxadiazole. (Compound 3).

Ethyl 4,5-dihydro-5-methyl-4-oxo-3-phenyl-i midazo[1,5-a]thieno-[3,2-e]pyrimidine-6-carboxylate, M.p. 268°–69° C. from 1,2,3,4-tetrahydro-3-methyl-2,4-dioxo-5-phenyl-thieno[2,3-d]pyrimidine and ethyl isocyanoacetate. (Compound 4).

4,5-dihydro-4-methyl-3-(5-methyl-1,2,4-oxadiazol-3-yl)-5-oxo-imidazo[1,5-a]thieno[2,3-e]pyrimidine m.p. 200°–201° C. from 1,2,3,4-tetrahydro-3-methyl-2,4-dioxo-thieno[3,2-d]-pyrimidine and 3-isocyanomethyl-5-methyl-1,2,4-oxadiazole. (Compound 5).

6-(5-cyclopropyl-1,2,4-oxadiazol-3-yl)-4,5-dihydro-5-methyl-4-oxo-3-phenyl-imidazo[1,5-a]thieno[3,2-e]pyrimidine, m.p. 235°–236° C. from 1,2,3-tetrahydro-3-methyl-2,4-dioxo-5-phenyl-thieno[2 3-d]pyrimidine and 5-cyclopropyl-3-isocyanomethyl-1,2,4-oxadiazole. (Compound 6).

6-(5-cyclopropyl-1,2,4-oxadiazol-3-yl)-5-ethyl-4,5-dihydro-4-oxo-3-phenyl-imidazo[1,5-a]thieno[3,2-e]pyrimidine, m.p. 190°–192°, from 3-ethyl-1,2,3,4-tetrahydro-2,4-dioxo-5-phenylthieno[2,3-d]pyrimidine and 5-cyclopropyl-3-isocyanomethyl-1,2,4-oxadiazole. (Compound 7).

EXAMPLE 3

3-(3-cyclopropyl-1,2,4-oxadiazol-5-yl)-4,5-dihydro-4-methyl-5-oxo-imidazo[1,5-a]thieno[2,3-e]pyrimidine Sodium (50 mg) was dissolved in dry ethanol (20 ml). Ethyl 4,5-dihydro-4-methyl-5-oxo-imidazo[1,5-a]thieno[2,3-e]-pyrimidine-3-carboxylate (0,55 g, 2 mmole), cyclopropanecarboxamide oxime (0,5 g, 5 mmole), and 5 g crushed mol. sieves 4 Å were added. The mixture was refluxed for 6 hours, then cooled to room temperature, where methylene chloride was added (30 ml). The mol. sieves were filtered off and the filtrate was reduced to 5 ml by evaporation in vacuo. Addition of water (25 ml) afforded a crystalline precipitate of the title compound which was collected by filtration. M.p. 215°–21° C. (Compound 8).

In a similar manner the following compounds were prepared:

4,5-dihydro-3-(3-methoxymethyl-1,2,4-oxadiazol-5-yl)-4-methyl-5-oxo-imidazo[1,5-a]thieno[2,3-e]pyrimidine, m.p. 206°–207° C. from ethyl 4,5-dihydro-4-methyl-5-oxo-imidazo-[1,5-a]thieno[2,3-e]pyrimidine-3-carboxylate and methoxyacetamide oxime. (Compound 9).

4,5-dihydro-4-methyl-3-(3-methyl-1,2,4-oxadiazol-5-yl)-5-oxo-imidazo[1,5-a]thieno[2,3-e]pyrimidine m.p. 263°–265° C. from ethyl 4,5-dihydro-4-methyl-5-oxo-imidazo[1,5-a]thieno-[2,3-e]pyrimidine-3-carboxylate and acetamide oxime. (Compound 10).

3-(3-ethyl-1,2,4-oxadiazol-5-yl)-4,5-dihydro-4-methyl-5- oxo-imidazo[1,5-a]thieno[2,3-e]pyrimidine, m.p. 212°–215° C., from ethyl 4,5-dihydro-4-methyl-5-oxo-imidazo[1,5-a]thieno-[2,3-e]pyrimidine-3-carboxylate and propionamide oxime. (Compound 11).

4,5-dihydro-5-methyl-6-(3-methyl-1,2,4-oxadiazol-5-yl)-4-oxo-3-phenyl-imidazo[1,5-a]thieno[3,2-e]pyrimidine, M.p. 58°–61° C. from ethyl 4,5-dihydro-5-methyl-4-oxo-3-phenylimidazo[1,5-a]thieno[3,2-e]pyrimidine-6-carboxylate and acetamide oxime. (Compound 12).

EXAMPLE 4 a. Ethyl 2-amino-thiophene-3-carboxylate was prepared by condensation of 1,4-dithiane-2,5-diol with ethyl cyanoacetate according to the literature.*

* K. Gewald, Chem.Ber. 98, 3571 (1965)

b. Ethyl 2-(N'-methylureido)-thiophene-3-carboxylate

To a stirred solution of ethyl 2-amino-thiophene-3-carboxylate (5,0 g, 29 mmol) and triethylamine (4,1 ml, 29 mmol) in dry tetrahydrofuran (100 ml) was added a 20% solution of phosgene in toluene (16 ml, 32 mmol). The mixture was heated to reflux for 3 h, then cooled to room temperature and exposed to a gaseous stream of methylamine for 10 min. After additional stirring for 30 min., the mixture was filtered and the filtrate was evaporated in vacuo, whereafter the crystalline residue was suspended in water, filtered off, and dried to give the title compound as colourless crystals, m.p. 127° C.

In the same manner ethyl 2-(N'-ethylureido)-thiophene-3-car boxylate, m.p. 83°–87° C., was prepared using ethylamine instead of methylamine in the above procedure.

c. 1,2,3,4-Tetrahydro-3-methyl-2,4-dioxo-thieno[2,3-d]-pyrimidine

A mixture of ethyl 2-(N'-methylureio)-thiophene-3-carboxylate (4,78 g, 21 mmol), 5% aqueous potassium hydroxide (80 ml), and 96% ethanol (80 ml) was stirred at room temperature for 2 h, whereafter acetic acid (40 ml) was added. The resulting mixture was stirred at 0° C. for 30 min., the precipitate filtered off and dried to give the title compound as colourless crystals, m.p. 315°–318° C.

In the same manner 3-ethyl-1,2,3,4-tetrahydro-2,4-dioxothieno[2,3-d]pyrimidine, m.p. 263°–265° C., was prepared from ethyl 2-(N'-ethylureido)-thiophene-3-carboxylate.

d. Ethyl 4,5-dihydro-5-methyl-4-oxo-imidazo[1,5-a]thieno-[3,2-e]pyrimidine-6-carboxylate The reaction was carried out under nitrogen.

SOLUTION A

To a stirred suspension of 1,2,3,4-tetrahydro-3-methyl-2,4-dioxo-thieno[2,3-d]pyrimidine (1,0 g, 5,5 mmol) in dry dimethylformamide thylformamide (25 ml) was added sodium hydride (55% in mineral oil dispersion, 0,31 g, 7., mmol). After stirring for 15 min. the solution was cooled to −30° C. and chlorodiethyl phosphate (1,0 ml, 7,1 mmol) was added. Then the solution was allowed to warm to room temperature, whereafter Solution B (see below) was added.

SOLUTION B

To a stirred solution of potassium t-butoxide (0,8 g, 7,1 mmol) in dry dimethylformamide (10 ml) at −30° C. was added ethyl isocyanoacetate (0,8 ml, 7,1 mmol). After stirring for 5 min., the solution was added to Solution A.

The final mixture was allowed to reach room temperature. Then acetic acid (3 ml) was added, and the solvent was removed in vacuo. The residue was partitioned between dichloromethane (25 ml) and 1M aqueous sodium hydroxide (25 ml). The organic layer was separated, dried over sodium sulfate and evaporated to give the title compound as colourless crystals, m.p. 191°–192° C. (Compound 13).

In a similar manner the following compounds were prepared:

6-(5-Cyclopropyl-1,2,4-oxadiazol-3-yl)-4,5-dihydro-5-methyl-4-oxo-imidazo[1,5-a]thieno[3,2-e]pyrimidine, m.p. 174°–176° C., from 1,2,3,4-tetrahydro-3-methyl-2,4-dioxo-thieno[2,3-d]pyrimidine and 5-cyclopropyl-3-isocyanomethyl-1,2,4-oxadiazole (Compound 14).

6-(5-cyclopropyl-1,2,4-oxadiazol-3-yl)-5-ethyl-4,5-dihydro-4-oxo-imidazo[1,5-a]thieno[3,2-e]pyrimidine, m.p. 154°–155° C., from 3-ethyl-1,2,3,4-tetrahydro-2,4-dioxo-thieno[2,3-d]pyrimidine and 5-cyclopropyl-3-isocyanomethyl-1,2,4-oxadiazole (Compound 15).

4,5-Dihydro-5-methyl-6-(5-methyl-I,2,4-oxadiazol-3-yl)-4-oxo-imidazo[1,5-a]thieno[3,2-e]pyrimidine, m.p. 221°–222° C., from 1,2,3,4-tetrahydro-3-methyl-2,4- dioxo-thieno[2,3-d]pyrimidine and 3-isocyanomethyl-5-methyl-oxadiazole (Compound 16).

EXAMPLE 5

4,5-Dihydro-5-methyl-6-(3-methyl-1,2,4-oxadiazol-5-yl)-4-oxo-imidazo[1,5-a]thieno[3,2-e]pyrimidine Sodium (50 mg) was dissolved in dry ethanol (50 ml). Ethyl 4,5-dihydro-5-methyl-4-oxo-imidazo[1,5-a]thieno[3,2-e]pyrimidine-6-carboxylate (0,4 g, 1,4 mmol), acetamide oxime (0.8 g, 11 mmol) and crushed molecular sieves 4 Å (5 g) were added. After the mixture had been refluxed for 8 h, an additional amount of acetamide oxime (0,4 g) was added and the heating was continued for 8 more hours. The mixture was then cooled to room temperature and dichloromethane (200 ml) was added. The molecular sieves were removed by filtration through a pad of celite, and the filtrate was evaporated in vacuo. The residue was suspended in water (20 ml) and the crystalline precipitate of the title compound was collected by filtration. M.p. 268°–270° C. (Compound 17).

In the same manner 6-(3-cyclopropyl-1,2,4-oxadiazol-5-yl)-4,5-dihydro-5-methyl-4-oxo-imidazo[1,5-a]thieno[3,2-e]pyrimidine, m.p. 218°–219° C., was prepared from ethyl 4,5-dihydro-5-methyl- 4-oxo-imidazo[1,5-a]thieno[3,2-e]pyrimidine-6-carboxylate and cyclopropan carboxamide oxime (Compound 18).

EXAMPLE 6

3-cyclopropYl-5-isocyanomethyl-1,2,4-oxadiazole a. 3-cyclopropyI-5-formylaminomethyl-1,2,4-oxadiazole A solution of ethyl formylaminomethyl-carboxylate (150 mmol) and cyclopropyl carboxamide oxime (100 mmol) in 100% EtOH (100 ml) was charged with Na (200 mg) and crushed molecular sieve (4Å) (10 g). The mixture thus obtained was stirred and heated to reflux for 8 hours. The mixture was cooled to room temperature, filtered through filter aid and the filtrate was evaporated in vacuo. The oily residue was partitionated into a CHCl3 phase which was dried with Na2SO4 and evaporated.

3-methyl-5-formylaminomethyl-1,2,4-oxadiazole, 3-ethyl-5-formylaminomethyl-1,2,4-oxadiazole, and 3-methoxymethyl-5-formylaminomethyl-1,2,4-oxadiazole were prepared in exactly the same manner from the appropriate carboxamide oximes.

b. 3-cyclopropyl-5-isocyanomethyl-1,2,4-oxadiazole

A stirred solution of 3-cyclopropyl-5-formylaminomethl-1,2,4-oxadiazole (60 mmol) and triethylamine (176 mmol) in CH2Cl2 (100 ml) was charged dropwise with POCl3 (60 mmol) at 0° C. The mixture was then left for 30 minutes with stirring at 0° C., whereafter a solution of Na2CO3 (60 mmol) in H2O (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 cm$^{-1}$. 3-ethyl-5-isocyanomethyl-1,2,4-oxadiazole was prepared from 3-ethyl-5-formylaminomethyl-1,2,4-oxadiazole in a similar manner. IR: cm$^{-1}$: 2170.

3-methyl-5-isocyanomethyl-1,2,4-oxadiazole was prepared from 3-methyl-5-formylaminomethyl-1,2,4-oxadiazole in a similar manner. IR: cm$^{-1}$: 2170.

3-methoxymethyl-5-isocyanomethyl-1,2,4-oxadiazole was prepared from 3-methoxymethyl-5-formylaminomethyI-1,2,4-oxadiazole in a similar manner. IR: cm$^{-1}$: 2170.

EXAMPLE 7

5-Cyclopropyl-3-isocyanomethyl-1,2,4-oxadiazole a. Formylaminomethyl-carboxamide oxime 0,55 mmol of freshly liberated hydroxylamine dissolved in 370 ml methano? was added to 53,6 g (0.638 mmol) N-formyl-amino-acetonitrile. An ice bath was used to keep the temperature below 20° C. during addition. The solution was allowed to stand at room temperature overnight, whereafter it was evaporated to give the title compound as pale crystals. Decomp. 104°–110° C.

b. 3-formylaminomethyl-5-ethyl-1,2,4-oxadiazole

A mixture of 35 ml ethylaoetate, 20 g formylaminomethylcarboxamide oxime, 1 g sodium and 30 g of crushed molecular sieve (4Å) was refluxed in 300 ml abs. EtOH for 8 hours whereafter a further 1 g sodium was added The reaction mixture was filtered and the filtrate was evaporated. The dark oily residue was suspended in 300 ml CHCl3, filtered and the filtrate was evaporated to give the title compound as an oil. H-NMR (60 MHz, CDCl3) (ppm): 1,4 (3H, t, J=8 Hz), 2,9 (2H, q, J=8Hz) 4,55 (2H, s) ,7,8 (1H, broad-NH), 8,25 (1H, s).

The following compounds were synthesized from the appropriate ethyl esters in a similar manner:

3-Formylaminomethyl-5-methyl-1,2,4-oxadiazole. H-NMR (60 MHz, CDCl3) (ppm); 2,6 (3H, s), 4,6 (2H, d, J=3 Hz), 7,4 (1H, broad-NH), 8,25 (1H, s).

3-Formylaminomethyl-5-methoxymethyl-1,2,4-oxadiazole H-NMR (60 MHz, CDCl3) (ppm): 3,5 (3H, s), 4,7 (4H, s+d, J=6 Hz), 7,8 (1H, broad-NH), 8,25 (H, s).

c. 5-cyclopropyl-3-formulaminomethyl-1,2,4-oxadiazole

O-cyclopropancarbonylformulaminoethanamidoxime (M=185, 3,13 mol, 1000 g, 58%) was dissolved in demineralized tap water (900 ml). O-cyclopropancarbonylformylaminoethanamidoxime was made by acylation of the oxime in acetone and contains triethylammonium chloride in the mol proportion 1:1.

The solution was refluxed for 4 h. It was checked by HPLC that the reaction was completed. The solution was cooled to 20° C., filtered, and the filtrate was extracted three times with 400 ml methylene chloride. The combined methylene chloride extracts were dried on sodium sulphate (120 g) at least 4 times with stirring.

The sodium sulphate was removed by decanting and filtration and the filtrate was evaporated to give the title compound as an oil. H-NMR (60 MHz, CDCl3) (ppm): 1,2 (4H, m) 2,8 (1H, m), 4,5 (2H, d, J=6Hz), 7,8 (1H, broad-NH), 8,2 (1H, s).

d. 5-Cyclopropyl-3-isocyanomethyl-1,2,4-oxadiazole

A stirred solution of 5-cyclopropyl-3-formylaminomethyl-1,2,4-oxadiazole (60 mmol) and triethylamine (176 mmol) in CH2Cl2(100 ml) was charged dropwise with POCl3 (60 mmol) at 0° C. The mixture was then left for 30 minutes with stirring at 0° C., whereafter a solution of Na$_2$CO$_3$(60 mmol) in H$_2$O (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 cm$^{-1}$.

5-Ethyl-3-isocyanomethyl-1,2,4-oxadiazole, 5-methyl-3-isocyanomethyl-1,2,4-oxadiazole, and 5-methoxymethyl-3-isocyanomethyl-1,2,4-oxadiazole were prepared in a similar manner. All compounds were oils and were characterized by their IR stretching band at 2160 cm$^{-1}$.

EXAMPLE 8

Methoxyacetamide oxime 2,3 g of sodium in 33 ml of dry methanol was mixed with 6,55 g of hydroxylamine hydrochloride in 66 ml of dry methanol. The mixture was filtered and 7,8 g of methoxyacetonitrile was added dropwise to the filtrate. The mixture was left for 48 hours. The mixture was then cooled to 4° C. Filtration and evaporation of the filtrate give 8,7 g of the title compound.

The following compounds were synthesized from the appropriate nitriles in an analogous manner:

Acetamide oxime
Propionamide oxime
Cyclopropane carboxamide oxime
Isopropyl carboxamide oxime
Isobutyramide oxime

We claim:

1. Heterocyclic compounds having the formula I

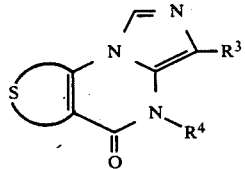
(I)

wherein
R$^3$ is

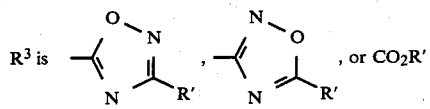

or CO$_2$R, wherein R' is
C$_{1-6}$-alkyl, C$_{3-7}$-cycloalkyl or C$_{1-6}$-alkoxymethyl; R$^4$ is C$_{1-6}$-alkyl;
—S— is

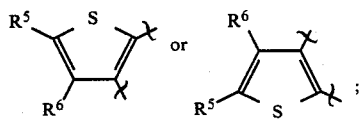

and wherein R$^5$ and R$^6$ independently are hydrogen, C$_{1-6}$-alkyl, or aryl.

2. A compound of claim 1 which is 3-(3-cyclopropyl-1,2,4-oxadiazol-5-yl)-4,5-dihydro-4-methyl-5-oxo-imidazo[1,5-a]-thieno[2,3-e]-pyrimidine 3. A compound of claim 1 which is 3-(5-cyclopropyl-1,2,4-oxadiazol-3-yl)-4,5-dihydro-4-methyl-5-oxo-imidazo[1,5-a]-thieno[2,3-e]pyrimidine.

4. A pharmaceutical composition suitable for use in the treatment of a central nervous system ailment associated with the benzodiazepine receptors comprising an amount of a compound of a compound of claim 1 which is effective for the alleviation of such disorder together with a pharmaceutically-acceptable carrier or diluent.

5. A pharmaceutical composition according to claim 4 wherein it is in the form af an oral dosage unit containing 1–100 mg of the active compound.

6. A method of treating a central nervous system ailment assoicated with the benzodiazepine receptors in a subject in need of such treatment comprising the step of administering to said subject an amount af a compound of claim 1 which is effective for the alleviation of such ailment.

7. A method of treating a central nervous system ailment associated with the benzodiazepine receptors in a subject in need of such treatment comprising the step of administering to said subject an amount af a compound of claim 1 which is effective for the alleviation of such ailment in the form af a pharmaceutical composition thereof, in which it is present together with a pharmaceutically-acceptable carrier or diluent.

* * * * *

UNITED STATES PATENT AND TRADEMARK OFFICE
CERTIFICATE OF CORRECTION

PATENT NO. : 4,866,065

DATED : Sep. 12, 1989

INVENTOR(S) : Frank Wätjen; Holger C. Hansen

It is certified that error appears in the above-identified patent and that said Letters Patent is hereby corrected as shown below:

Column 2, line 34; "R'-C(C=NOH)NH$_2$" should read
-- R'-C(=NOH)NH$_2$ --.

Column 4, line 29; "the oontrol value." should read -- the control value.--.

Column 4, line 43; "solubilizing Oil and" should read
-- solubilizing oil and --.

Column 6, line 8; "like, t he carrier" should read
-- like, the carrier --.

Column 6, line 42; "pharmaceuticallyacceptable" should read
-- pharmaceutically-acceptable --.

Column 7, line 21; "carboxylate" should read -- carboxylate, --.

Column 8, line 33; " 0,8 g 55%" should read -- 0,87 g 55% --.

Column 8, line 48; "acid wa added" should read -- acid was added --.

Column 8, lines 59-60; "3-phenyl-i midazo" should read
-- 3-phenyl-imidazo --.

Column 9, line 4; "[2   3-d]" should read -- [2,3-d] --.

Column 9, line 29; "215°-21°C." should read -- 215-217°C. --.

Column 9, line 49; "M.p. 58°-61°C." should read
M.p. 258-61°C. --.

Column 9, line 51; "carboxyIate" should read -- carboxylate --.

UNITED STATES PATENT AND TRADEMARK OFFICE
CERTIFICATE OF CORRECTION

PATENT NO. : 4,866,065
DATED : Sep. 12, 1989
INVENTOR(S) : Frank Wätjen; Holger C. Hansen It is certified that error appears in the above-identified patent and that said Letters Patent is hereby corrected as shown below:

Column 10, lines 4-5 "car boxylate" should read
-- carboxylate --.
Column 10, line 32; "dry dimethylformamide thylformamide (25 ml)" should read -- dry dimethylformamide (25 ml) --.
Column 10, line 66; "methyI-6-(5-methyI-I,2,4" should read
-- methyl-6-(5-methyl-1,2,4 --.
Column 11, line 31; "3-cyclopropYl" should read
-- 3-cyclopropyl --.
Column 11, line 34; "3-cyclopropyI" should read
-- 3-cyclopropyl --.
Column 11, line 53/54; "-formylaminomethl-" should read
-- -formylaminomethyl- --.
Column 11, line 58/59; "50 mI)" should read -- 50 ml) --.
Column 12, line 5/6; "-formylaminomethyI-" should read
-- -formylaminomethyl- --.
Column 12, line 23; "ethylaoetate," should read
-- ethylacetate, --.
Column 12, line 27; "was added The reaction" should read
-- was added. The reaction --.
Column 12, line 61; "4H, m) 2,8" should read -- 4H, m), 2,8 --.
Column 14, line 4; delete "$R^3$ is".
Column 14, line 8; delete "or $CO_2R$,"

UNITED STATES PATENT AND TRADEMARK OFFICE
CERTIFICATE OF CORRECTION

PATENT NO. : 4,866,065
DATED : Sep. 12, 1989
INVENTOR(S) : Frank Wätjen; Holger C. Hansen It is certified that error appears in the above-identified patent and that said Letters Patent is hereby corrected as shown below:

Column 14, line 30; "of a compound of a compound" should read -- of a compound --.

Column 14, line 34; "form af an oral" should read -- form of an oral --.

Column 14, line 39/40; "amount af a compound" should read -- amount of a compound --.

Column 14, line 45/46; "amount af a compound" should read -- amount of a compound --.

Column 14, line 47; "form af a pharmaceutical" should read -- form of a pharmaceutical --.

Signed and Sealed this

Twenty-third Day of October, 1990

Attest:

HARRY F. MANBECK, JR.

*Attesting Officer*  *Commissioner of Patents and Trademarks*